United States Patent [19]
Niedermeyer

[11] Patent Number: 5,864,890
[45] Date of Patent: Feb. 2, 1999

[54] UNDERGARMENT BRIEFS

[76] Inventor: William P. Niedermeyer, 1024 Mt. Mary Dr., Green Bay, Wis. 54311

[21] Appl. No.: 889,461

[22] Filed: Jul. 8, 1997

Related U.S. Application Data

[63] Continuation-in-part of Ser. No. 797,172, Feb. 10, 1997, abandoned.

[51] Int. Cl.$^6$ .............................. A41B 9/00; A41B 9/02; A41B 9/12; A41B 13/04
[52] U.S. Cl. ...................... 2/403; 2/405; 2/408; 2/243.1; 604/385.1
[58] Field of Search ................................. 2/79, 83, 227, 2/400, 401, 402, 403, 404, 405, 406, 407, 408, 409, 111, 78.2, 69, 69.5; 604/385.1, 385.2, 386, 387, 388, 389, 390, 391, 392, 393, 394, 395, 396, 397, 398

[56] References Cited

U.S. PATENT DOCUMENTS

| | | | |
|---|---|---|---|
| 620,317 | 2/1899 | Hatch | 2/408 |
| 1,414,203 | 4/1922 | Redmond | 2/408 |
| 1,540,557 | 6/1925 | McLoughlin | 2/408 |
| 1,774,724 | 9/1930 | Rankin | 2/408 |
| 1,834,780 | 12/1931 | Hutchinson | 2/408 |
| 1,973,963 | 9/1934 | Nishimoto | 2/408 |
| 2,476,585 | 7/1949 | Cohen | 2/408 |
| 5,014,364 | 5/1991 | Orr | 2/408 |
| 5,499,404 | 3/1996 | Marchiorello | 2/403 |

*Primary Examiner*—Jeanette Chapman

[57] ABSTRACT

An undergarment including waist and leg apertures and openable front panel with a closure. The undergarment including similarly shaped overlapped superposed half width segments bonded to each other in preselected area to form front and rear panels having a crotch area. The garment also includes non-bonded overlapped portions forming two halves of an openable front panel connected at the top of the opening by a tape. The rear panel overlapped segments are bonded together. Reusable tapes are also used to attach the segments halves together in the front panel. The rear panel includes flap extensions protruding from each side margin and the extension attach to the side margins of the front portion. The garment is folded in the crotch region.

18 Claims, 2 Drawing Sheets

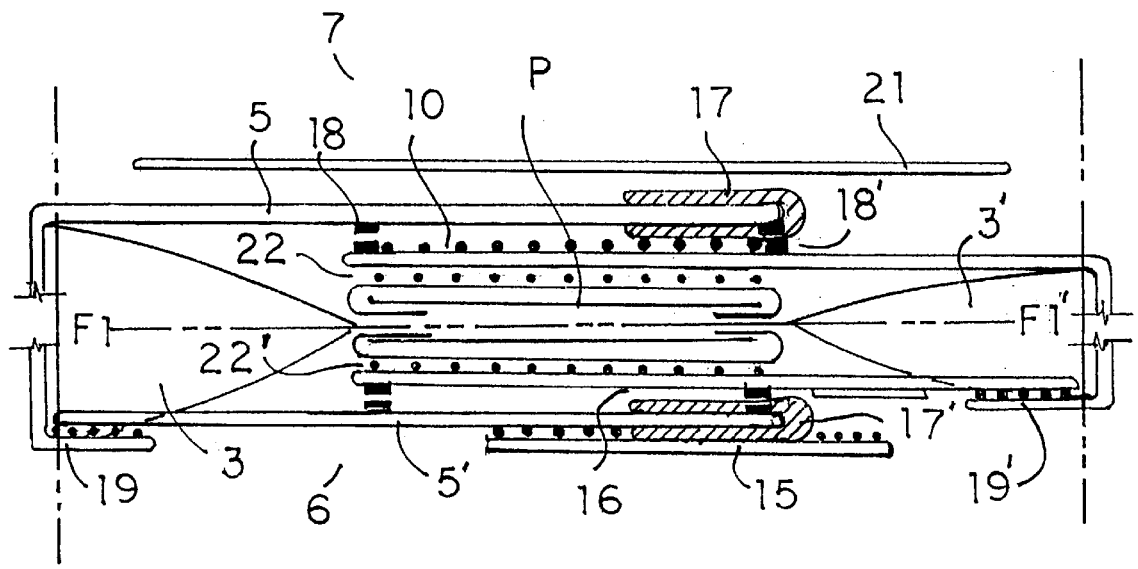
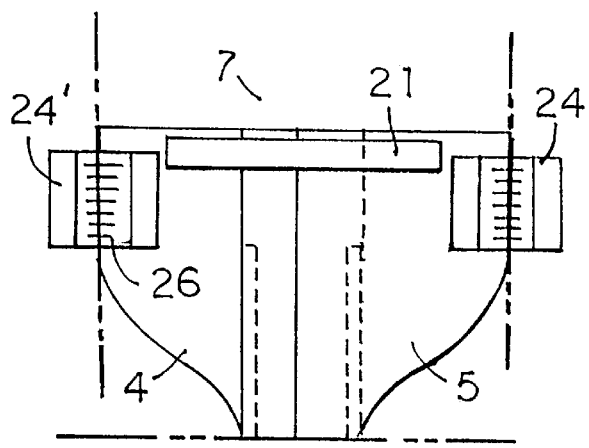
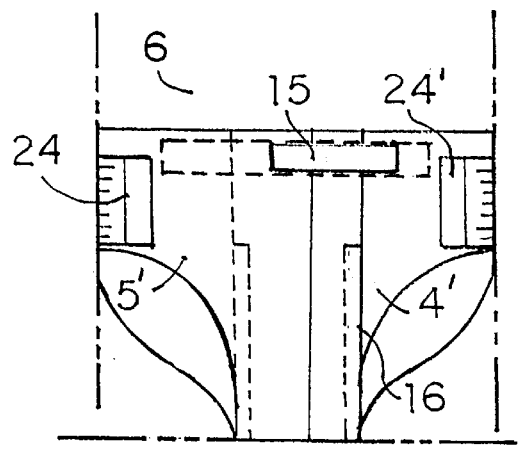

UNDERGARMENT BRIEFS

This application is a continuation-in-part of application Ser. No. 08/797,172 filed Feb. 10, 1997, now abandoned.

FIELD OF THE INVENTION

This invention relates to a garment useful to infants, children and adults as an undergarment. More specifically, these garments are manufactured from continuous webs with or without an absorbent pad as an integral part thereof, or the garment can include an adhesive zone with release strip which is removed for attachment of a pre-selected pad of the user's choice, for example, a preferred brand of hygienic pad for feminine use.

Garments of this invention are referred to as underpants or briefs for adults, or training pants for young children, and with an absorbent pad attached inside, as protective panties for feminine use or incontinent briefs for adult use.

The inventive product differs from state of the art incontinent products by providing a front opening feature that allows the user to more easily pull the garment upward over his knees for securement around the waist.

While some known incontinent products are expandable so they can be applied while the user is standing, the opening feature of the instant invention allows application to the wearer in the manner of conventional textile garments such as trunks, shorts and pants, with closure tapes provided for snug fastening around the waist.

BACKGROUND OF THE INVENTION

This application for a U.S. Patent is a continuation-in-part of U.S. application Ser. No. 08/797,172 for garments having front and rear panels connected along a minimum of three margins, at least two of which include extension flaps on each side margin of one panel being folded over and attached to the other panel.

Products constructed according to '172 can include garment types as diverse as pants, shirts, vests, gowns, undershorts and underbriefs, etc.

This continuation-in-part application describes the preferred embodiment as a garment for use without an absorbent pad, thus providing only limited absorbency and protection. The basic garment is referred to hereinafter as 'briefs'.

In a second embodiment, the briefs are constructed so that they will accept a separate commercially available feminine pad, or in another embodiment are manufactured as an incontinent brief complete with absorbent pad of conventional design, including pervious covering against the user, absorbent core, and impervious covering attached to the inside surface of the brief.

Briefs heretofore described in prior art (Class 2—garments) are normally made from textile fabrics, and being hand sewn or knitted as unitary items, are formed or assembled to have full width front and rear panels, contiguous if knitted, or joined by sewn seams along side margins. Features can include front openings for male urinary functions, but with an expandable continuous elastic waistband rather than an openable panel. Panties for women and underwear for male use have similar construction.

U.S. Pat. No. 1,329,119 is one of the first to describe baby pants with an inner non-porous lining, and having buttons instead of tapes to connect front and rear panels at the top side margins. Patent '119 also shows the general 'hourglass' shape so prevalent in state of the art diapers.

The baby pants of '119 are made from textile cloth but had many of the useful features and functional components of current diapers including leg cutouts, front rear and intervening crotch sections, waistband drawstrings instead of waistband elastic, buttons instead of side connector tapes, impervious lining pervious absorbent pad and impervious barrier, leg drawstrings versus leg elastics, etc., but the essential element for absorbency was missing until later.

In the intervening 50 plus years, many new materials, adhesives, elastics, absorbent fluff, absorbent additives, pervious barrier sheets and nonwoven fabrics with improved hand and surface treatment, as well as improved manufacturing techniques based on fabrication of continuous webs have transformed baby garments from hand sewn textile products with an impervious liner to state of the art diapers, briefs, and incontinent products.

The prior art in U.S. Class 128 for sanitary napkins and Class 604 for diapers is replete with examples of the abovementioned improvements and features including the hourglass shape of U.S. Pat. No. 3,461,871 to Foote (1963) and U.S. Pat. No. 3,368,562 to Vogt (1968) and the important addition of leg elastics per U.S. Pat. No. 3,860,003 to Buell.

Thus, while substantial prior art exists for absorbent diaper features, there is scant teaching on incontinent pants or briefs with panel openings that make it easier for the user to put the briefs on, be openable for urinary functions, and with the front 'fly' open, and be easily dropped to the user's knees for excretory functions.

U.S. Pat. No. 4,944,733 describes a diaper with a front opening for use in toilet training or for use by incontinent adults wherein the absorbent padding layer (28) is located between the inner layer (19) and outer layer (24), and is held therein by secure attachment of the inner and outer layers 19 and 24 respectively around their entire periphery. The product of '733 thus defines a product having the absorbent pad as part of a garment requiring difficult manufacturing manipulations with a front opening that must be closed by transverse movement of bias cut flaps to the overlapped position.

U.S. Pat. No. 4,615,695 to Cooper describes a combination diaper training pant with the typical hourglass shape, but it also includes absorbent material between the inner pervious sheet and the outer impervious material, again being limited to a product with an integral absorbent pad. Patent '695 shows a front opening in both the front impervious panel and the inner pervious absorbent padding.

In the instant invention, a front opening is constructed by longitudinally overlapping half width webs with the advantage that one or both of the marginal edges (flaps) can be enclosed with folded strips that define a 'reinforced' front fly without further processing of materials except along longitudinal lines until the product is assembled and ready for separation into discreet units, thus being well adapted for high speed fabrication.

SUMMARY OF THE INVENTION

The briefs of this invention are formed by advancing two webs, each equal to about one half of the product width plus a few inches in superposed partially overlapped relationship along a longitudinally extending central zone.

A selected portion of the overlapped region is bonded together so that equal and opposite segments form a unitary rear panel.

The non-bonded front panel portion of the overlap forms a 'fly' opening which allows the briefs to be opened when the user puts them on.

A recloseable tape secures the openable front panel for use, and may remain closed for male urinary use.

In another embodiment, a selected portion of the inside surface of the inside half panel can be adhesively coated and covered with a removeable release strip when a commercially available pad is added to the briefs.

In still another embodiment, the absorbent pad is formed to become an integral part of the brief wherein the brief and the absorbent pad each can have elasticized elements for substantially equal co-acting contraction as a unitary combination product.

Other advantages and objects of the invention may be seen in the ensuing specification.

BRIEF DESCRIPTION OF THE DRAWINGS

FIG. 5 is a top sectional view of elements viewed from line 5—5 of FIG. 1.

FIG. 6 is an elevation view of the brief looking at the rear panel.

FIG. 7 is an elevation view of the brief viewed looking at the front panel illustrating the use of elasticized tapes to connect front and rear panels.

DETAILED DESCRIPTION

Figure 1:
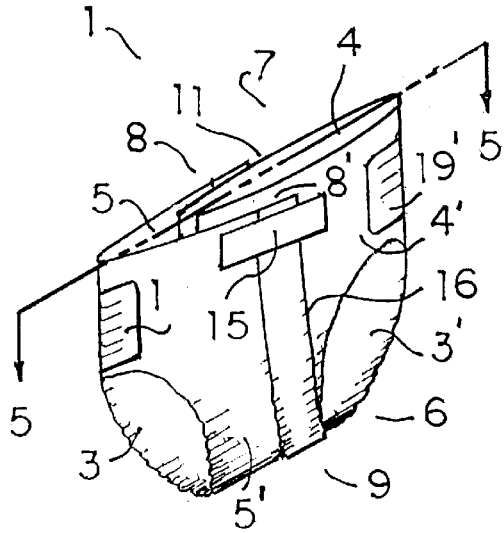
FIG. 1 is a perspective view of the brief embodying the preferred elements as applied to the wearer.

In FIG. 1, garment 1, referred to hereinafter as briefs, is shown as worn and includes a waist aperture 2 and leg apertures 3 and 3'.

The briefs 1 are comprised of a first half panel segment 4 having a width substantially equal to one half of the garment width plus the amount of overlap between first segment 4 and second segment 5.

In the manufacturing process, segment 5 (still in web form before being cut into discreet briefs) is advanced along a path, and the other segment (still in web form) is superposed on top (see FIG. 2) and advanced along the same path.

After certain fabricating steps later described, the two overlapped segments 4' and 5' together with connecting tape 15 form the front panel 6 and are folded along line F1-F1' to be joined to the rear panel 7 with folded extensions 19 and 19' and adhesively secured to the opposite panel—in this case front panel 6.

In FIG. 1 the overlap between opposing half segments can be seen as at 8 on the rear panel and 8' between segments at the top of the front panel.

Figure 2:
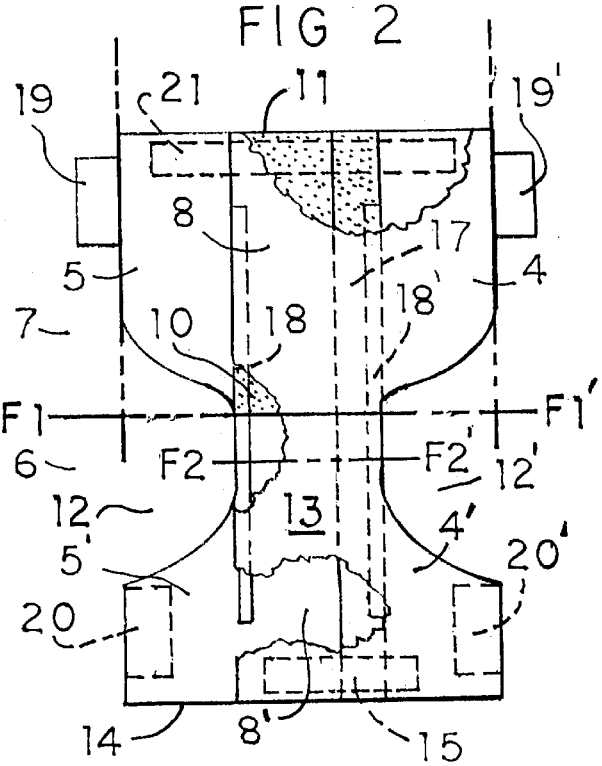
FIG. 2 is a partially fragmented plan view of the inventive brief in an unfolded configuration.

In FIG. 2, front panel 6 comprising the tape connected half width segments 4 and 5 is folded (upward in the illustration) around fold line F1-F1' and after being secured at the side margins defines the basic shape of FIG. 1 including the leg and waist apertures.

The crotch section formed by the above-mentioned folding straddles line F1-F1', as designated by numeral 9 in FIG. 1.

Referring again to FIG. 2, an area 8 of adhesive 10 is applied between half segments 4 and 5 in the overlapped central region. The adhesive area extends longitudinally from top margin 11 of rear panel 7 (see FIG. 1) to a fold line F1-F1', however, it is within the scope of this invention that the adhesive can be applied beyond F1-F1' to lower portions of what becomes the front panel (6 of FIG. 1).

In FIG. 2, fold line F1-F1' is shown equidistant from the top margins of both front and rear panels, and if unequal longitudinal panels are preferred, the transverse fold can be made around F2-F2' located at any position along minimum width central portions 13 of the the overlap in crotch area 9.

The central area 13 in the front panel between cutouts 12 and 12' is defined by the unbonded overlapped area between first segment 4' and second segment 5' extending from F1-F1' to the top margin 14 of front panel 6.

Without adhesive bonding between segments 4' and 5', flaps on the 'fly (not referenced for clarity) are held together with closure tape 15 near the top margins to facilitate later transverse folding of both segments as a unitary front panel.

In FIG. 1, the unbonded central area (13 of FIG. 2) between segments of the front panel defines the front opening 16.

The major portion of closure tape 15 is affixed to segment 5' near the top, and the free end extends over segment 4'. For opening and subsequent reclosing operations, the free end can be coated for easier release and later closure against a receptor area (not shown) on segment 4'.

Figure 3:
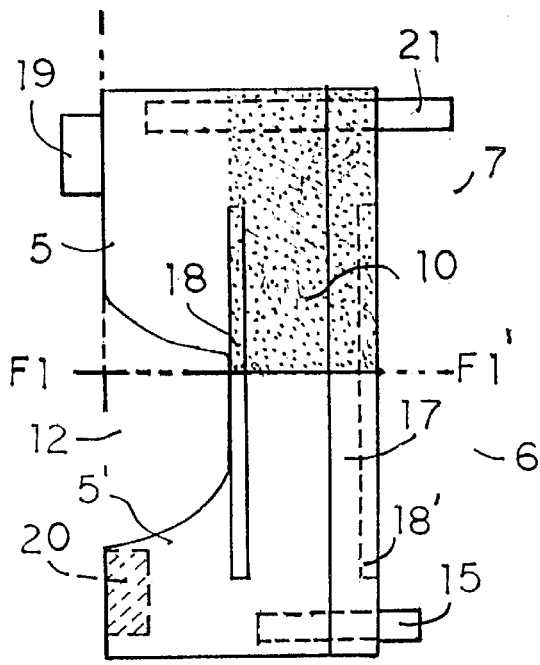
FIG. 3 is a plan view illustrating one of two shaped segments used to construct the briefs of FIGS. 1 and 2.

In FIGS. 1,2, and 3, a V-folded reinforcing strip 17 is adhesively bonded to both sides of front panel segment 5', and if preferred the linear longitudinal margin of segment 4' can also be reinforced.

Figure 4:
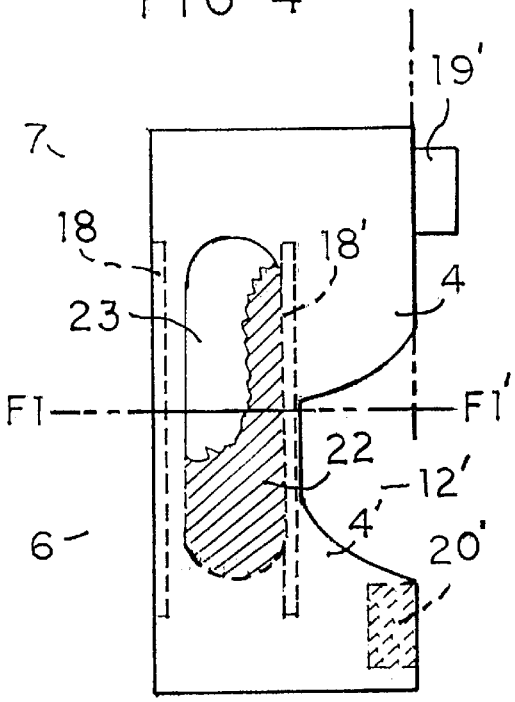
FIG. 4 is a plan view illustrating the other shaped segment used in cooperating assembly with the segment of FIG. 3.

In FIGS. 2, 3, and 4, longitudinally oriented elastic strips 18 are shown in the contracted state. In the manufacturing process they are applied under tension and adhesively attached to the segments in pre-selected discontinuous areas.

In FIG. 3, 'leg elastic' segment 18' is shown in phantom since it is covered by folded reinforcing strip 17.

Being applied to segment 5 and therefore on the outermost ply of the brief, gathering and shirring of the material will occur as illustrated in FIG. 1 when the web is transversely cut and the elastic contracts to its untensioned state, as in FIGS. 2, 3, and 4.

Relaxed elastic strips 18 and 18' are shown in FIG. 4 to indicate that they can be added to segment 4 if it is beneficial to have the inside ply shirred for comfort or fit.

In FIGS. 1 through 4, flaps 19 and 19' are extended from each half segment, and after the two tape connected half segments are folded along F1-F1', the flaps are overfolded and bondably secured to receptor areas 20 and 20' on opposite segment portions of the front panel.

In FIG. 3, a shrinkable elastic strip 21 is attached near the top margin of the rear panel to define a contractable waistband. It is noted that the contractable waistband, and placement of the closure tape at different locations of the receptor area, both serve to enhance circumferential waist fitting of the garment.

A heat shrinkable waistband strip 21 is preferred since transverse contraction of the rear panel would prevent margins of the folded front panel from lining up with the side margins of the rear panel prior to foldover and attachment of the side flaps 19, 19'.

In FIG. 4, an ovular area of adhesive 22 can be applied to the inside surface of the inside segment 4 for attachment of an absorbent pad by the user after the cover release strip 23 is removed to expose the adhesive.

In FIGS. 1 through 4 and in FIGS. 6 and 7, the side flaps 19, 19', 24, 24' and receptor areas 20, 20' are shown spaced from the top margins of the segments in order to keep adhesively covered receptor areas away from transverse end margins which are later cut by die rolls or equivalent means. This spacing provision is required to sustain high manufacturing efficiencies.

The sectional illustration of FIG. 5 is viewed looking from the waist aperture toward the folded crotch, with all components referenced as in previous iillustrations.

Both leg apertures 3, 3' are shown substantially symmetrical about fold line F1-F1', but for sake of clarity, the left hand rear panel segment 5 and left hand front panel segment 5'; are spaced apart greater than 4 and 4', causing side flap 19 to have a different length than 19' only for sake of illustration.

In FIG. 5, rear panel 7 is comprised of segment portions 4 and 5 adhesively bonded in overlapped area 10.

Front panel 6 is comprised of segment portions 4' and 5' and the overlap remains unbonded.

A single reinforcing strip 17 is applied to an edge of segment 5 and the space 16 between the reinforcing strip and panel segment 4' of the front panel illustrates the front opening feature (see 16 of FIG. 5).

In FIG. 5, an absorbent pad P is folded along line F1-F1' and attached to the inside surface of inner half segments 4 and 4' with adhesive in areas 22 and 22' respectively.

The absorbent pad can be inserted and attached by the wearer after a cover strip 23 (see FIG. 4) is removed. Details of pad construction are not shown, but it is understood that many desireable features described in prior art can be readily incorporated in a pad manufactured as an integral part of the described briefs.

FIG. 6 illustrates rear panel 7 comprised of half segments 4 and 5. For better snugness around the waist, tapes 19 and 19' of FIGS. 1 through 5 are replaced by tapes 24, 24' having central portions 26 elasticized.

FIG. 6 shows the tapes 24, 24' extended from the rear panel but not yet folded to entrap the front panel. It is within the scope of this invention to use VELCRO (hook and loop) fasteners instead of adhesively fastened tapes.

FIG. 7 illustrates a completed brief with a reinforced front opening 16, closure tapes 24, 24', waistband strip on the rear panel (shown phantom) and longitudinal leg elastics (also phantom).

In FIG. 5, an integral pad would include an impervious barrier strip 25 folded around side edges of pad P to avoid leakage.

When manufactured without a pad, a barrier 25 can be bondably attached to the inside surface of the briefs with adhesive 22.

While in the foregoing specification a detailed description has been set forth for the purpose of illustration, many variations can be made in the details stated herein without departing from, or limiting, the spirit and scope of the invention.

It is within the scope of the invention to define other arrangemtns and embodiments according to the claims made hereinafter:

I claim:

1. A garment having a waist encircling aperture and leg apertures between front and rear panel portions secured by fastening means and a front panel opening comprising:

first and second shaped segments each having a length equal to twice a distance between a top of a garment waist and a bottom of a garment crotch and a width substantially equal to a width of the garment, said first and second shaped segments superposed in a partially overlapped mirror, image orientation, forming overlapped first and second segments and inner most and outermost segments, said overlapped mirror image orientation defining a longitudinally extending area of said garment, an overlapped area, said shaped segments including curvilinear cutouts from each segment along longitudinal side margins most remote from said overlapped area, said rear panel including said first and second segments bonded together in a preselected portion of said overlapped area, said front panel opening defined by non-bonded overlapped portions of said superposed segments in said longitudinally extending area, said overlapped first and second segments folded along a line between front and rear waist margins, fastening means including an extension of each segment protruding from a non-overlapped side margin of said rear panel folded and attached to the same segment adjacent a side margin of the front panel to form said leg apertures and said waist aperture, at least one central fastening means attached to said first segment of said front panel for securement of said first and second segments at a top of said front panel opening.

2. The garment of claim 1 wherein said protruding side extensions are spaced from transverse end margins of said front and rear panels.

3. The garment of claim 1 wherein a longitudinal margin of at least one of said overlapped segments nearest the overlapped area is enclosed within a V-folded strip.

4. The garment of claim 1 wherein the overlapped segments include spaced longitudinal portions with margins and wherein elastic members are bondably secured along spaced longitudinal portions of the margins of said overlapped segments.

5. The garment of claim 4 wherein at least one margin and one of said elastic members is enclosed by a V-folded strip.

6. The garment of claim 1 wherein said overlapped first and second segments are folded along a line not equidistant between front and rear panel waist margins.

7. The garment of claim 1 wherein said protruding side extensions are tapes bondably attached to opposite side margins of said first and second segments on said rear panel for attachment respectively to said first and second segments of said front panel on opposite sides of said front panel opening.

8. The garment of claim 1 wherein said preselected bonded portion between overlapped segments extends between lower portions of the overlapped segments of said front panel.

9. The garment of claim 1 wherein said central fastening means have at least one end with protruberances that attach to a receptor area.

10. The garment of claim 1 wherein at least a portion of said central fastening means is elastic.

11. The garment of claim 1 wherein said central fastening means is attached to a receptor area having release coating.

12. The garment of claim 1 including a release coated strip and an underlying adhesive area for attachment of an absorbent pad to an inner surface of said overlapped area.

13. The garment of claim 1 including an absorbent pad bondably secured along a substantial portion of its length to the innermost segment in a portion of an overlapped folded crotch area.

14. The garment of claim 13 wherein said absorbent pad contains elastic members secured to portions of said pad along lines parallel to a major dimension of said pad.

15. The garment of claim 13 wherein said absorbent pad includes an impervious fluid barrier folded over side margins of said pad.

16. The garment of claim 1 wherein said garment has an impervious material bonded to an inside of the innermost segment.

17. The garment of claim 1 including a transversely oriented strip of shrinkable material secured adjacent a waist margin of said rear panel.

18. The garment of claim 1 wherein said first and second segments are two-ply laminates of permeable and impervious material and said permeable ply forms an inside surface of said segments.

* * * * *